United States Patent [19]

Change, Jr.

[11] Patent Number: 4,615,209

[45] Date of Patent: Oct. 7, 1986

[54] MULTI RANGE IMPULSE HAMMER

[76] Inventor: Nicholas D. Change, Jr., 7514 Hatillo Ave., Canoga Park, Calif. 91306

[21] Appl. No.: 688,518

[22] Filed: Jan. 3, 1985

[51] Int. Cl.⁴ .................. G01N 3/30; G01M 7/00; G01P 15/09

[52] U.S. Cl. .................................... 73/12; 73/DIG. 4

[58] Field of Search ............... 73/12, 82, 572, 582, 73/573, 584, 588, 862.68, DIG. 4

[56] References Cited

U.S. PATENT DOCUMENTS

| | | | |
|---|---|---|---|
| 3,421,364 | 1/1969 | Moneypenny et al. | 73/82 |
| 4,030,339 | 6/1977 | Yakshin et al. | 73/12 |
| 4,422,320 | 12/1983 | Moorby et al. | 73/12 |
| 4,505,153 | 3/1985 | Lilley et al. | 73/862.68 X |

FOREIGN PATENT DOCUMENTS

| | | | |
|---|---|---|---|
| 0082028 | 6/1980 | Japan | 73/12 |
| 0939988 | 6/1982 | U.S.S.R. | 73/12 |

*Primary Examiner*—Charles A. Ruehl
*Attorney, Agent, or Firm*—Robert A. Marrs

[57] ABSTRACT

An impulse hammer of a variable sensitivity type permitting the user to instantly select from at least three different full scale operational ranges which includes an elongated handle having a plastic grip at one end and a head carried at its other end normal thereto. A head extender is detachable carried on one end of the head while a force sensor terminating in an impact tip is fixedly carried on the opposite end. An electrical circuit couples to a transducer in the force sensor and communicates through the head and handle with a coaxial connector located at the end of the handle. An impedance converter is included in the circuit transforming the high impedance signal from the transducer to a low impedance output voltage. A manual selector switch changes the voltage gain of the sensor to avoid amplification of noise level.

4 Claims, 4 Drawing Figures

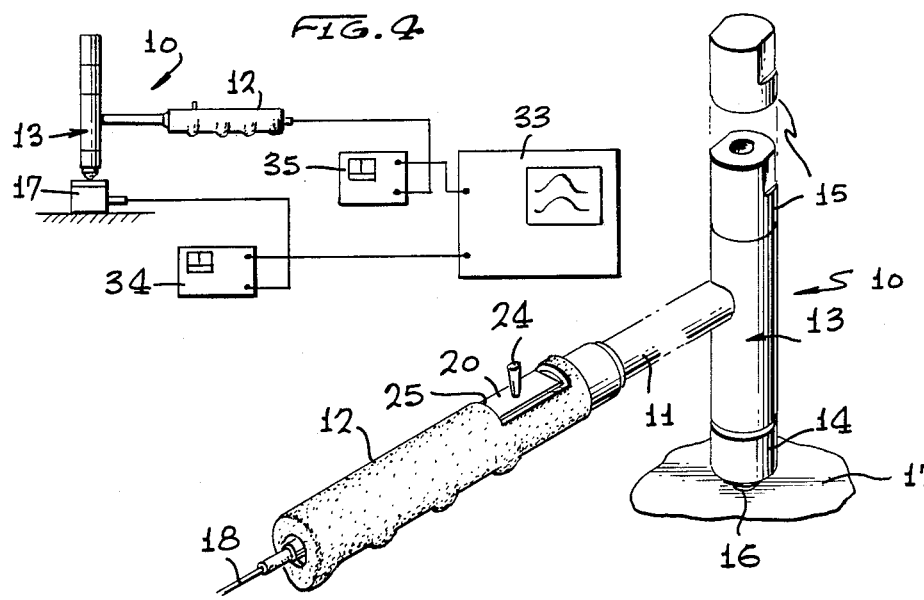
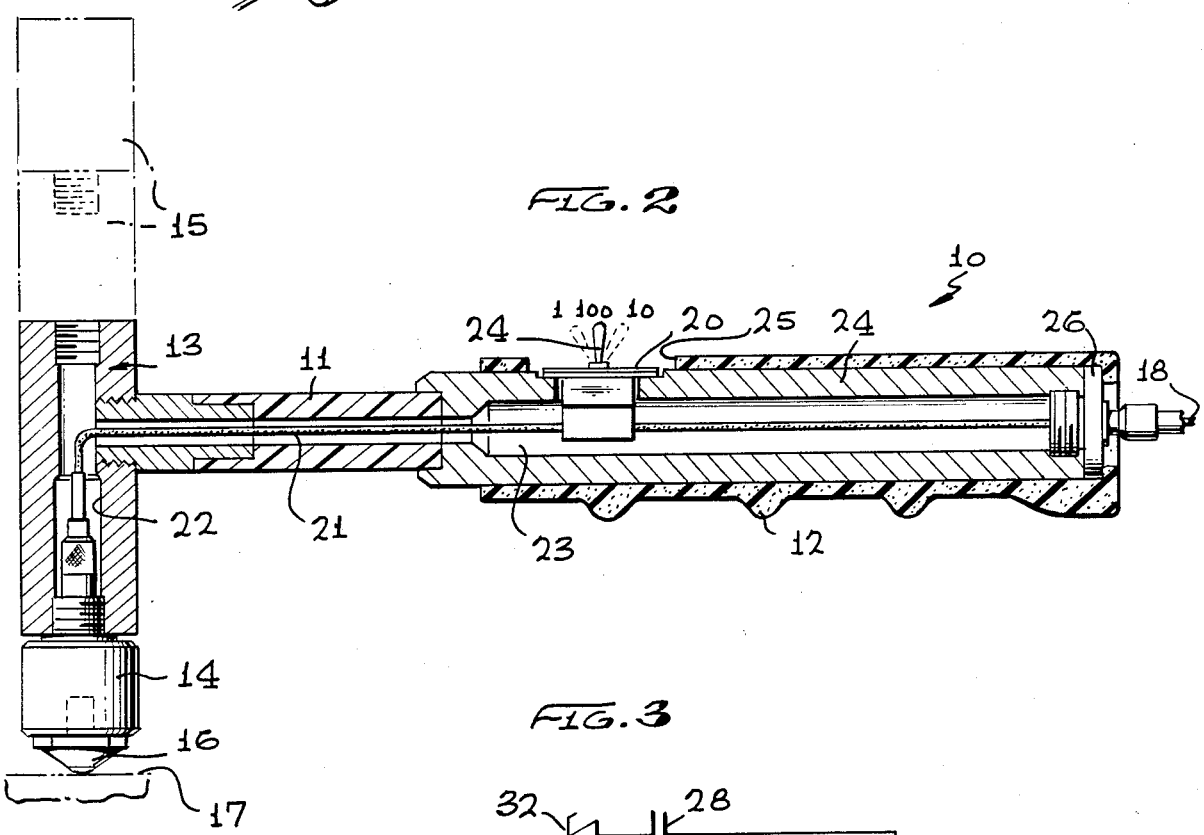
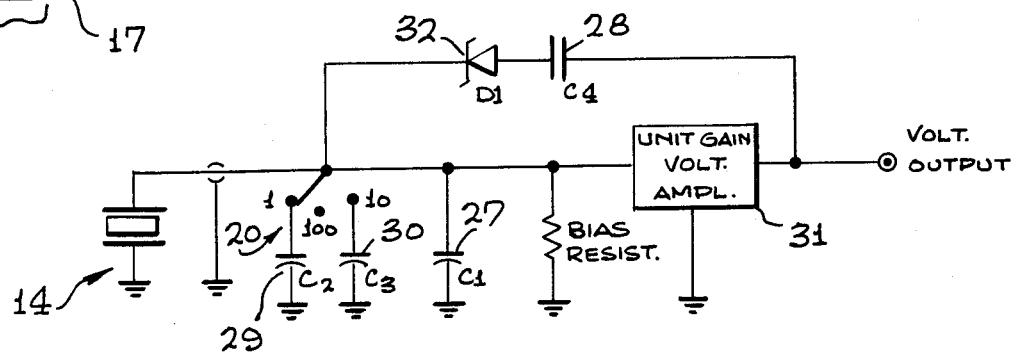

MULTI RANGE IMPULSE HAMMER

BACKGROUND OF THE INVENTION

1. Field of the Invention

The present invention relates to the field of impulse hammers and, more particularly, to a novel such hammer incorporating means for allowing manual switching between a selection of operational ranges.

2. Brief Description of the Prior Art

In the past, impulse hammers have been used to shock structures and machines into motion for the purpose of analyzing behavior in terms of frequency characteristics. Impulse hammers incorporate rigid quartz for sensors mounted in a head carried on the end of a handle in order to produce output voltages exactly analogous to force pulses created when a test structure is struck by the hammer. The generated voltage pulse defines mathematically the input or "forcing" function. Resultant motion is sensed by accelerometers mounted elsewhere on a test structure and, in some instances, spectrum analyzers, computers and other instrumentation are responsive to these output signals so as to perform modal analysis, graphically display transfer functions and to search for destructive or annoying resonances.

Difficulties and problems have been encountered when employing conventional impulse hammers which stem from the fact that three or more different hammers are often necessary in order to cover a dynamic range of operation. For example, depending upon the size of the test structure, forces as low as one pound or as high as 5,000 pounds may be necessary for optimum results. Also, difficulties have been encountered in conventional hammers wherein the cable or wiring from the load cell transducer in the head of the instrument or hammer is generally external and is cumbersome, makes the handling of the instrument difficult to use. With some prior impact hammers, a gain amplifier is employed which determines the hammer sensitivity and thus the range of the device. Such a practice is not conducive to accuracy inasmuch as undesired noise levels are magnified or amplified and cause distortion in the ouptut signal. Still further problems with conventional impulse hammers reside in the lack of overload protection to prevent adding more negative feedback from affecting discharge time constants and compromising pulse fidelity.

Therefore, a long standing need has existed to provide an improved impulse hammer having selection means for deriving a plurality of sensitivity selections within a wide range of force inputs so as to eliminate the need for different fixed range hammers. Also, a need is present to provide a sensitivity means in an impulse hammer which is not dependent on a gain amplifier which would normally amplify noise levels and which would provide overload protection for the circuit involved.

SUMMARY OF THE INVENTION

Accordingly, the above problems and difficulties are obviated by the present invention which provides a novel multi range impulse hammer which includes an elongated handle having a rubber or plastic grip at one end and a head fastened at its other end in a position normal to the longitudinal axis of the handle. One end of the head includes a load cell or transducer for initiating a signal in response to impact of an impact tip upon a structure and electrical circuit means therefore is internally cabled from the transducer through the head and handle terminating in a coaxial connector positioned in the end of the handle. The electrical circuit means includes a manually operated selector for obtaining different hammer sensitivities via two values of chip capacitors coupled in parallel with an existing capacitor. In one version, the handle is connected to the head with a fiber glass extension for eliminating unwanted resonance in the pass band.

Therefore, it is among the primary objects of the present invention to provide a novel multi range hammer for applications requiring a wide range of force inputs which provides a selector means for deriving a variety of hammer sensitivities so as to eliminate the user stocking three or four different fixed range hammers.

Another object of the present invention is to provide a novel multi range hammer having means for adjusting hammer sensitivity which does not depend upon a gain amplifier.

Still another object of the present invention is to provide a novel multi range impulse hammer incorporating an overload protection feature which provides a threshhold voltage block to prevent adding more negative feedback to the circuit which further reduces voltage gain below unity and which incorporates a capacitor that prevents diode leakage from affecting discharge time constant and compromising pulse fidelity.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

FIG. 1 is a perspective view showing the novel multi range impulse hammer of the present invention;

FIG. 2 is a longitudinal cross-sectional view of the multi range impulse hammer shown in FIG. 1;

FIG. 3 is a circuit diagram employed in the hammer shown in FIGS. 1 and 2; and

FIG. 4 is a diagrammatic view showing a typical instrumented use of the impulse hammer incorporating the present invention.

DESCRIPTION OF PREFERRED EMBODIMENT

The multiple range impulse hammer of the present invention is illustrated in the general direction of arrow 10 which includes an elongated handle 11 having a vinyl or plastic-like grip 12 at one end which terminates at its opposite end in a head 13 which is mounted so that its longitudinal central axis is normal to the longitudinal central axis of the handle 11. A force sensor 14 is detachably connected to one end of the head 13 while a weighted extender or extenders 15 are carried on the opposite end of the head 13. An impact tip 16 is mounted on the extreme end of the force sensor 14 and is intended to impact or forcibly engage with a structure 17 for the purpose of structural excitation. The hammer 10 contains the force sensor which is a transducer at the forward or striking end of the head 13. In one form, the transducer may be a piezo-electric force sensor which produces a voltage output signal exactly analagous to the force impulse produced as the structure is struck.

This signal contains all of the frequency, amplitude and phase information necessary to exactly define the impulse mathematically, usually by the use of a spectrum analyzer, computer or the like. A coax cable 18 conducts the signal from the sensor 14 through the head 13 and handle 11 for interconnecting with test and display instrumentation.

The impulse hammer 10 is a variable sensitivity type having a three-position miniature toggle switch 20 located on the handle which allows the user to instantly select from three different full scale ranges. The sensitivities available are 1, 10 and 100 mV/lb.F for ranges 5000, 500, and 50 lb. force full scale.

Referring now in detail to FIG. 2, it can be seen that the transducer in the force sensor 14 is interconnected with the switch 20 and the table 18 by means of an internal cable 21 that passes through internal bores in the head 13 as identified by numeral 22 and an internal passageway or bore 23 provided in the handle 11. Such construction insures that the cabling 21 is internal and that there are no external loops, wires, leads or the like which will interfere with the operation and convenience of handling the hammer. Also, it can be seen that the plastic grip 12 surrounds an enlarged portion of the handle identified by numeral 24 and that the switch 20 includes an actuating arm 24 that protrudes through an opening 25 in the grip 12. A section of the handle 11 between the head 13 and the enlarged portion 24 is of reduced diameter or thickness and is composed of a fiber glass material. The end of the handle 11 includes mounting of a coaxial connector 26 having a peripheral edge portional region thereof covered by the material of the grip 12.

The impact tip 16 transmits the force of the hammer strike into the sensor 14 and protects the sensor face from damage. Interchangeable impact tips of various materials such as steel, aluminum and plastic are used to shape the rise time, and thus the frequency content of the output pulse. Various lengths and material extenders 15 may be used so as to allow the user to alter the mass of the head and thus change the width of the pulse thereby changing the total energy of the pulse.

Referring now in detail to the circuit diagram of FIG. 3, it can be seen that the three-position switch 20 changes the voltage gain of the transducer or sensor 14 whereby amplification of noise level is completely eliminated. This is achieved by changing the signal gain by switching various values of capacitors across the transducer or load cell. By adjusting switch arm 24 to one of three positions two different values of chip capacitor are placed in parallel with an existing capacitor identified by numeral 27. Capacitors 29 and 30 represent the other capacitors which are selected by the switch 20. Therefore, three different hammer sensitivities are available. Using the electrostatic equation, $V = Q/C$, one can see that by simply varying capacitance C, the voltage V is made to vary inversely with charge Q the independent variable. Charge Q is produced by the load cell such as a quartz sensor without a conventional built-in amplifier and the charge Q is exactly analagous to impact force. The charge is converted to voltage V by total shunt capacitance C. The impedance level is reduced 10 orders of magnitude by a unity gain FET (field effect transistor) source follower amplifier 31 which is operably carried beneath the switch 20 as shown in FIG. 2.

Capacitor 28 and Zener diode 32 constitute an overload protection circuit that prevents force overloads from damaging components of the amplifier 31. These components are connected from the input gate to the output source of the impedance converting amplifier 31. The diode provides a threshhold voltage block to prevent adding more negative feedback to further reduce voltage gain below unity and the capacitor, being an indefinite resistance to DC, prevents diode leakage from affecting discharge time constant and compromising pulse fidelity. When the diode voltage exceeds nine volts, it will bleed charge away from the gate and build up into the capacitor 28, the other end of which is fixed to the voltage supply since the gate can withstand 100 volts so that ample protection margin is provided.

The overload protection feature is especially important in the multi-range hammer, since the user can switch from the 5000 pound F range to the 50 pound F range with the flick of his thumb. On the latter range, the load cell 14 would produce 5000 times 0.100 or 500 volts if shocked by mistake at the 5000 pound F level.

Referring now in detail to FIG. 4, a means is shown for calibration of the impact hammer by employing dynamic means since the force of the strike is generated by the momentum of the entire head while the force measured by the force sensor 14 is that created by the mass behind the sensor only. The mass in front of the sensor that is, the impact tip, will change the effective sensitivity of the hammer and hence the necessity for dynamic calibration. One method of dynamic calibration commonly used involves the striking of a calibrated force transducer with the hammer. Comparing the dynamic force signals from the force transducer and the hammer 10 on a storage oscilloscope 33 will provide a valid hammer calibration. Most accurate results are obtained by the use of a digitizing storage oscilloscope. Power units are indicated by numerals 34 and 35.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A multi-range impulse hammer comprising the combination of:
an elongated handle having a grip at one end and an elongated head secured to its other end in a position normal to the longitudinal axis of said handle;
a selected end of said head carrying a load cell transducer for initiating a signal in response to impact upon a structure undergoing test;
electrical circuit means internally cabled from said transducer through said head and said handle to terminate in a coaxial connector at said one end of said handle;
said electrical circuit means includes a manually operated selector for obtaining a variety of different impact sensitivities; and
said selector includes at least two values of chip capacitors coupled in parallel with a standard capacitor.

2. The invention as defined in claim 1 including:
a fiberglass sleeve interconnecting said other end of said handle with said head for eliminating unwanted resonance in said signal.

3. The invention as defined in claim 2 wherein:
said selector includes a manual selector switch operable to change the voltage gain of said transducer to avoid amplification of noise level.

4. The invention as defined in claim 3 wherein:
said electrical circuit means includes an impedance converter operable to transform a high impedance output signal from said transducer to a low impedance output voltage signal.

* * * * *